United States Patent [19]

Davis

[11] Patent Number: 5,011,579

[45] Date of Patent: Apr. 30, 1991

[54] NEUTRAL OIL RECOVERY PROCESS FOR THE PRODUCTION OF NAPHTHENIC ACIDS

[75] Inventor: Gerald E. Davis, Berry, Ala.

[73] Assignee: Merichem Company, Houston, Tex.

[21] Appl. No.: 465,445

[22] Filed: Jan. 16, 1990

[51] Int. Cl.$^5$ .......................... B01D 3/06; B01D 3/34
[52] U.S. Cl. ..................................... 203/37; 159/2.1;
 159/49; 203/72; 203/73; 203/88; 203/89;
 560/100; 562/490
[58] Field of Search .................... 203/14, 37, 72, 73,
 203/88, 89; 159/2.1, 49; 562/490; 560/100

[56] References Cited

U.S. PATENT DOCUMENTS

| | | | |
|---|---|---|---|
| 2,039,106 | 4/1936 | Nelson et al. | 203/37 |
| 2,085,287 | 6/1937 | Bailey | 203/37 |
| 3,525,777 | 8/1970 | Johnson et al. | 203/37 |
| 3,923,644 | 12/1975 | Hindman | 159/2.3 |
| 3,968,002 | 7/1976 | Standiford | 159/13.2 |
| 4,225,394 | 9/1980 | Cox et al. | 203/37 |
| 4,227,020 | 10/1980 | Zeinalov et al. | 562/511 |

OTHER PUBLICATIONS

"Napthenic Acid"; Edgar S. Lower; *Specialty Chemicals*, vol. 7, No. 2, pp. 76-82.
"Recover Napthenic Acids Continuously"; D. B. Todd and F. C. Rac; reprinted from *Hydrocarbon Processing*, Aug. 1967.

*Primary Examiner*—Virginia Manoharan
*Attorney, Agent, or Firm*—Kirk & Lindsay

[57] ABSTRACT

A process for treating naphthenic fractions with a caustic blend of sodium and potassium hydroxide, preflashing the naphthenic fraction to remove water and then flashing the dewatered fraction to remove the neutral oils and the materials that were not formed into the acid salts. The naphthenic salt mixture is then quenched and acidified so as to recover the naphthenic acids. Naphthenic acids recovered from the process of the present invention have acid numbers which are generally higher than the naphthenic acids heretofore produced from the corresponding feed streams. The process provides for the flashing of the water which otherwise would cause foaming and not permit the recovery of the acid salt for the enhanced separation of the naphthenic acids.

8 Claims, 1 Drawing Sheet

NEUTRAL OIL RECOVERY PROCESS FOR THE PRODUCTION OF NAPHTHENIC ACIDS

FIELD OF THE INVENTION

The present invention is directed to a process for the removal of neutral oil and other impurities from a naphthenic fraction. More specifically, the process of the present invention recovers naphthenic acids having higher acid numbers than heretofore possible. In a specific aspect it is directed to a process which involves treating the naphthenic fraction with a caustic blend of sodium hydroxide and potassium hydroxide, preflashing the mixture to remove water, flashing to remove the neutral oils from the mixture and quenching and acidifying the naphthenic acid salt to spring the acid and separating the naphthenic acid.

BACKGROUND OF THE INVENTION

Naphthenic acids and their derivatives are discussed in the article "Naphthenic Acid" by Edgar S. Lower, published in *Specialty Chemicals*, Vol. 7, No. 2, pages 76-82. This article sets forth the chemical and physical properties of naphthenic acids as well as the various procedures for the refining and purification of these acids. The article further discloses the general uses of naphthenic acids as being applicable in soap, in paint driers, extreme pressure additives for lubricating oils or greases, or as a chemical intermediate and solvent. Heretofore, naphthenic acids have been recovered by distillation. However, since the naphthenic acids often boil in the same range as other hydrocarbons having similar molecular weight their separation is with large amounts of contaminants or undesirable components and accordingly of low acid number.

A process for removing naphthenic acids from refinery streams by caustic washing is disclosed in an article, "Recover Naphthenic Acids Continuously" by David B. Todd and Frank C. Rac reprinted from *Hydrocarbon Processing*, August 1967. This process is based on continuous acidification followed by simultaneous centrifugal separation.

SUMMARY OF THE INVENTION

The present invention is directed to a process for treating naphthenic fractions with a caustic blend of sodium and potassium hydroxide, preflashing the naphthenic fraction to remove water and then flashing the dewatered fraction to remove the neutral oils and the materials that were not formed into the acid salts. The naphthenic salt mixture is then quenched and acidified so as to recover the naphthenic acids. Naphthenic acids recovered from the process of the present invention have acid numbers which are generally higher than the naphthenic acids heretofore produced from the corresponding feed streams. The process provides for the flashing of the water which otherwise would cause foaming and not permit the recovery of the acid salt for the enhanced separation of the naphthenic acids.

BRIEF DESCRIPTION OF THE INVENTION

Figure 1:
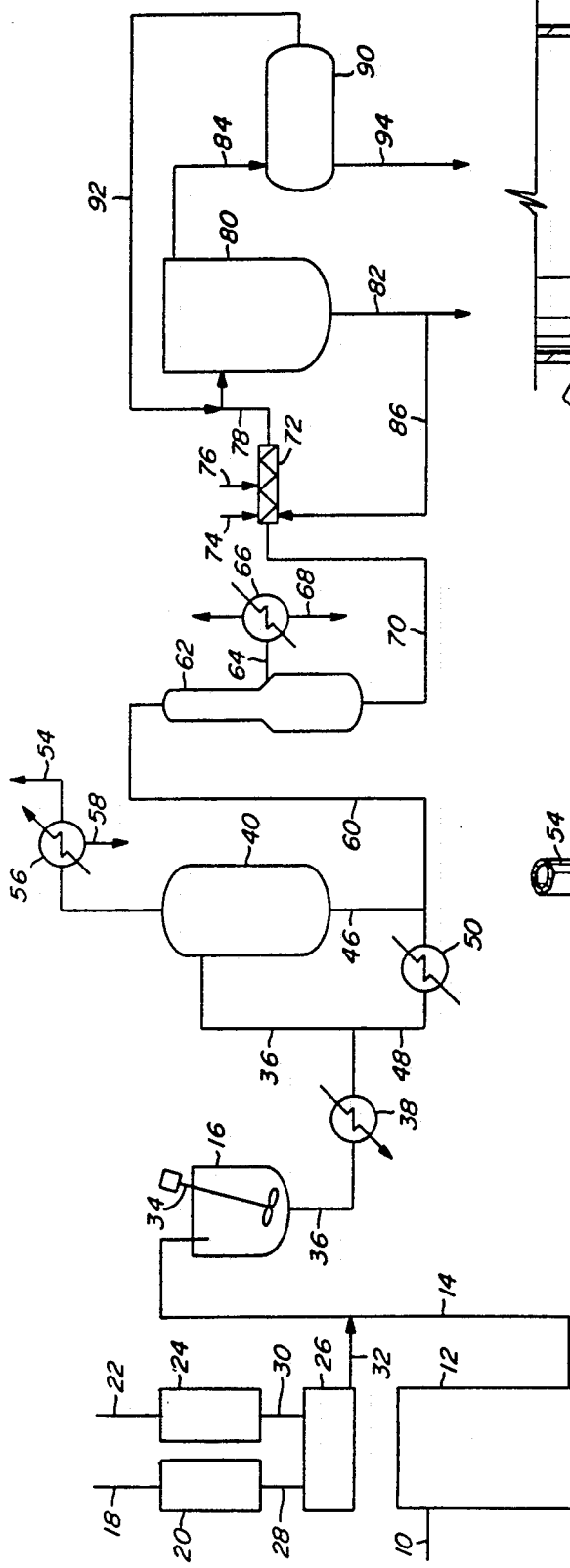
FIG. 1 is a block flow diagram of the process of the present invention.

Referring now to FIG. 1, a crude naphthenic acid containing fraction which may be either a kerosene fraction which has an end point up to about 550° F. or a diesel fraction which has a higher end point than 550° F. is introduced by line 10 to a crude holding vessel 12. The crude fraction will contain besides the naphthenic acids, phenolics, neutral oils and sulphur compounds. This mixture is taken by line 14 and introduced into a mixing vessel 16. To the crude fraction is added a mixture of sodium hydroxide and potassium hydroxide. Sodium hydroxide is introduced by line 18 into a vessel 20 whereas potassium hydroxide is introduced by line 22 into a vessel 24. The two hydroxides or caustic solutions may be mixed as a blend in vessel 26 by taking sodium hydroxide from vessel 20 by line 28 and potassium hydroxide by line 30 to blend a mixture in vessel 26. The potassium hydroxide makes up at least 35% of the mixture and preferably between 40 and 50% of the mixture. The use of the potassium hydroxide is to maintain the naphthenic acid salt in soluble form throughout the process. The blend of hydroxide may be added to line 14 through line 32 or directly to the mixing vessel 16 wherein the hydroxides in the crude fraction containing the naphthenic acid are thoroughly mixed. A mixer 34 may be used to accomplish the mixing.

The amount of total hydroxide as a blend of sodium and potassium hydroxide added to the crude faction containing the naphthenic acids is sufficient so that between 65 to 90% and preferably 70 to 80% of the naphthenic acid is formed as the alkaline metal salt or naphthenate.

The mixing of the blend of sodium and potassium hydroxide with the fraction containing the naphthenic acid is carried out under the following conditions:

Temperature range: 80 to 140° F.
Pressure: atmospheric approximately
pH: reduced from 12 or greater to about 9
mixing: sufficient to form the naphthenate The mixture is then removed from vessel 16 by line 36 wherein the mixture is heated in exchanger 38 in heat exchange with steam to a temperature between 275° and 315° F. and preferably between about 285° to 300° F.

This mixture which is removed from vessel 16 and is heated in heat exchanger 38 contains water or is a "moist" mixture as a result of the water that may be in the caustic solutions as well as water formed in the reaction of the hydroxides with the naphthenic acids producing the naphthenates in the naphthenate stream. A substantial portion of the heated mixture is the alkali salt of the naphthenic acid or the naphthenate. It has been found that the presence of water causes severe foaming in the handling of this mixture and causes a severe problem to the removal of the contaminants from this mixture. The process of the present invention has overcome this problem. It has been found that a key to the removal of the moisture is to remove the moisture before it is incorporated in the bulk liquid to flash water from the moist naphthenate stream at a temperature above 360° F. to produce a dewatered naphthenate stream. Accordingly, the "moist" mixture is introduced to a preflash vessel 40. The process of the present invention was not perfected until a preflash of the water from the mixture using a thin film was developed which prevented foaming. Further, with the water removed, a more effective and controlled flash of the neutral oils and other contaminants is possible from the dewatered naphthenate stream and naphthenic acids of high acid number are produced. Naphthenic acids having acid numbers of greater than 300 are now possible according to the process of the present invention.

Figure 3:
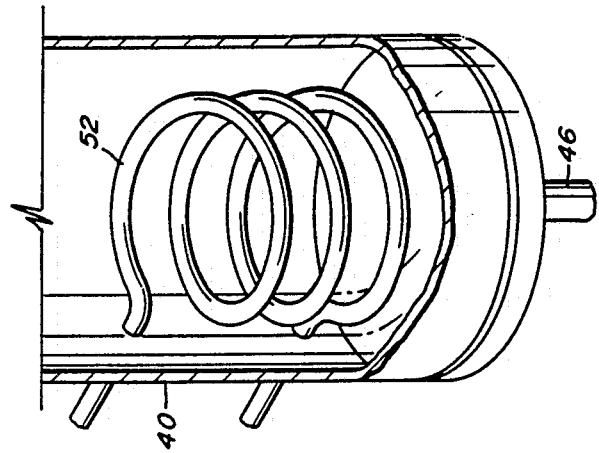
FIG. 3 shows the lower portion of the preflash vessel with a heating coil.
Figure 2:
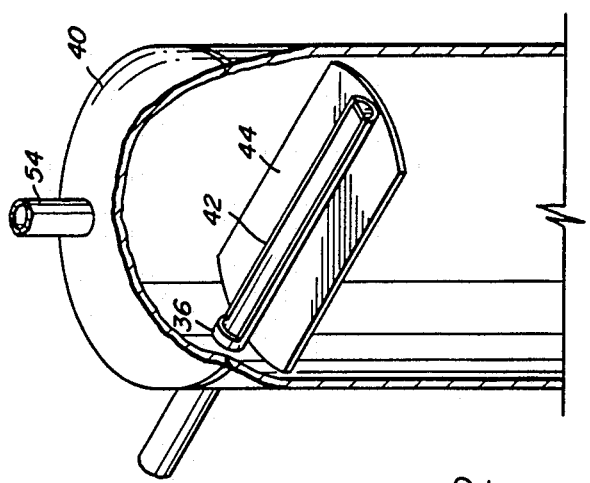
FIG. 2 shows the details of the upper portion of the preflash vessel of a preferred embodiment of the present invention.

Referring to FIG. 2, a preferred arrangement for providing a thin film regime for carrying out the removal of the water is illustrated. The heated mixture is introduced by line 36 which is a pipe which enters the top portion of vessel 40. The pipe 36 extends essentially the diameter of the vessel 40 and may be configured at its end in various forms such as half the pipe being cut away as shown at 42. The end of the pipe or distributor, which is preferably closed so that the heated mixture overflows, is situated above a plate 44 which may be of any configuration such as circular or rectangular but which has an area approximately one-half that of the cross-sectional area of the vessel 40. The heated naphthenate mixture is introduced onto the flat plate 44 which provides a thin film regime for the evaporation of water in the mixture. The vessel 40 is maintained under vacuum with the conditions being under a vacuum of about 11.5 to 12.5 pounds per square inch absolute (PSIA) or about 25 inches absolute of mercury (Hg). As set forth hereinabove, the mixture is heated in heat exchanger 38 to a temperature within the range of about 285° to 315° F.; however, by means of a recycle, which will be explained hereinafter in more detail, the liquid from the cutaway portion 42 of pipe 36 onto plate 44 is maintained at a temperature of about 360° to 390° F. Liquid is removed from the bottom of vessel 40 by line 46 and a portion thereof is recycled by line 48 passing through a heat exchanger 50. The liquid taken from vessel 40 by line 46 has a temperature within the range of about 380° to 400° F., for example about 395° F. Steam is introduced to one side of heat exchanger 50 to heat that portion of the recirculated material to temperatures above 400° F. and in the range of about 400° to 415° F. by adjusting the recycle rate and temperature of the recycled material in line 48. The effective temperature of the inlet material to vessel 40 can be maintained within the temperature range of 370° F. to 390° F. Vessel 40 may also contain a heating coil or steam coil 52 in the bottom of the vessel, as shown in FIG. 3, so that the material in the vessel is maintained at temperatures in the range of 390° to 400° F.

It has been found that the mixture in line 36 is temperature sensitive as it enters vessel 40 and is distributed on plate 44. A temperature below 350° F. causes severe foaming. It is therefore necessary to maintain the temperature of the naphthenate mixture in line 36 at the distributor or cut away portion 42 at above 360° F. Not only is temperature controlled but a thin film regime is provided so that the water is removed easily and quickly. A vacuum is drawn on vessel 40 by any suitable vacuum means through line 54. A condenser 56 is in the line 54. Water and some of the neutral oils and other materials removed through line 54 are condensed and removed from the condenser 56 by line 58.

The non-recirculated liquid from the preflash vessel 40 is taken by line 60 into a flash vessel 62. In this operation or vessel 62, the removal of the contaminants is in a thin film regime. This can be accomplished in several ways including a wiped film evaporator, a falling film evaporator or any other like device. A preferred vessel 62 is a falling film evaporator. The naphthenate mixture is introduced by line 60 into the top of vessel 62 wherein the liquid will run down a plurality of tubes. A vacuum is pulled on the vessel through line 64. A condenser 66 is in line 64 wherein the neutral oils, that small portion of the naphthenic acid that has not been formed as the naphthenate and other materials are condensed and removed by line 68. The conditions in vessel 62 are as follows:

Temperature: 480 to 500° F.
Pressure: 0.2 to 0.77 PSIA (vacuum)

From the bottom of flash vessel 62 is removed a high purity naphthenate stream by line 70.

The high purity naphthenate, with the phenolics, sulphur containing materials and other contaminants removed, is a naphthenate having less than 1.5% contaminants. This naphthenate of high purity may be stored or transported as the naphthenate. It is preferred, however, to produce the high purity naphthenic acid so the naphthenate mixture in line 70 is introduced to a quenching and springing vessel 72. The vessel 72 may be simply a pipe having good mixing therein or a special device for reconstituting the naphthenate into naphthenic acid. Water is introduced at the inlet by line 74. Thereafter, sulfuric acid is introduced by line 76 which enables the reaction of the acid to reconstitute the naphthenate into the naphthenic acid with the formation of a mixed sodium-potassium sulphate brine. The addition of the water is to quench the mixture to a temperature of about 160° F. from the higher temperatures which the mixture is at in the flash vessel 62. The amount of sulfuric acid added is sufficient to bring the solution to a pH of about 2 to 3. The acidified mixture is then taken by line 78 to a decanter 80. In decanter 80 the acid brine solution is removed by line 82 and the reconstituted naphthenic acid is removed by line 84.

It has been found advantageous to recirculate a portion of the acid brine from line 82 by line 86 for reintroduction to the quenching and springing vessel 72. This aids in stabilizing the pH and obtaining a good mixture within the vessel 72. Likewise, the reconstituted naphthenic acid may be introduced into a second vessel 90 where further acid brine is separated and recirculated by line 92 and the purified naphthenic acid is removed by line 94.

The process as described hereinabove produces a high purity naphthenic acid which has an acid number which is substantially higher than the corresponding naphthenic acid which may be recovered by distillation from a naphthenic fraction. One factor is that the contaminants are reduced to much lower levels than can be obtained by distillation and also the neutral oils which have essentially the same boiling points can be removed and separated from the naphthenic acids. To illustrate the advantages of the process of the present invention, naphthenic acids from a diesel treater are compared to a typical analysis of the materials obtained by the process of the present invention. The naphthenic acid from a diesel treater is identified as "B" whereas the analysis of a material obtained from the present invention is identified as "A". Typical analysis are as follows:

|   | Unsaps | Phenolics | PT Sulphur | Tan |
|---|--------|-----------|------------|-----|
| B | 12%    | 0.4%      | .05%       | 190 |
| A | 0.9%   | 0.1%      | .01%       | 220 |

It is seen by the above that the typical acid number (Tan) is 220 as compared to 190 for a comparable naphthenic fraction being treated in a diesel treater. This significant increase in acid number enhances the value of the naphthenic acids so that lower value diesel fraction treated naphthenic acids may be used in situations where only the higher valued naphthenic acid obtained from kerosene fractions have been used. Using the process of the present invention with kerosene fractions, and more specifically, the treatment of the overhead stream derived from distilling contaminants away from naphthenic acids as is the current standard method of contaminant removal. This overhead stream contains a relatively lighter fraction or lower molecular weight of naphthenic acid along with neutral oils, phenolics and sulfur compounds. Naphthenic acids having acid numbers in excess of 300 such as within the range of 300 to 330 are obtained by subjecting this distillation overhead stream as the feed to the process of the present invention, enabling the use of these naphthenic acids in situations where only synthetic acidic materials have been used. Naphthenic acids have not been obtained heretofore with acid numbers in these ranges. It is to be understood that depending on the feed stock that the process enables products to be produced which have typical acid numbers from 220 to 330 all with contaminants of less than 1.5%.

Using the numbering of lines and equipment shown in FIG. 1, specific examples run in a pilot-unit having the configuration of FIG. 1 is set forth as follows:

EXAMPLE 1

A crude naphthenic acid containing fraction, 21552#, was introduced into line 14. The fraction contained 14009# naphthenic acid, 5388# neutral oils (unsaps), 431# water and 1724# phenolics. The fraction was at a temperature between 60° and 120° F. and a pressure between 50 and 75 PSIA. To this fraction was added a mixture of sodium and potassium hydroxide, 2007#, of which 40% was potassium hydroxide. The mixture was at a temperature of between 60° and 90° F. and a corresponding pressure between 50 and 75 PSIA. Of the mixture, 1003# was water. These were introduced and mixed in a mixing vessel 16 at atmospheric pressures and at temperatures ranging from 80° to 140° F. The mixed stream was heated in heat exchanger 38 to temperatures within the range of 285° to 300° F. and the pressure was raised to between 20 and 30 PSIA. To the heated stream was added the recycle stream 48, 94236#, which is a portion of the material from preflash vessel 40. The stream introduced to the preflash vessel 40 is maintained at temperatures between 360° and 390° F. The pressure within the preflash vessel 40 is between 11.9 and 12.3 PSIA or a slight vacuum. Removed overhead by line 54, 3341#, is mostly water, 1348#, and neutral oil 1347# as well as some phenolics, 431# and some naphthenic acid, 215#. The bottom stream, 20218#, is removed by line 60 and introduced with a falling film evaporator 62 at temperatures within the range of 480° to 500° F. and a pressure of between 0.2 and 0.77 PSIA. The material removed in vacuum line 64 and condensed, 7746#, contains neutral oils (unsaps), 3851#, naphthenic acid, 2579#, phenolics, 1273# and only a small amount of water, 43#. The naphthenate stream removed from the flash vessel 62 is essentially all naphthenate, 11215#, containing some neutral oils (unsaps), 190#, and phenolics, 20#. This stream may be stored or preferably is quenched with water, 2235#, and acidified with sulfuric acid, 15105#, of which water, 376#, is a part of the solution. The acidified mixture, 119078#, is introduced into a decanter 80 and the acid brine is removed by line 82, 22137#, which is mostly water. A purified naphthenic acid stream is removed from second vessel 90 by line 94, 12015#, which is essentially naphthenic acid, 11215#, containing water, 590#, neutral oils (unsaps), 210# and a small amount of phenolics, 20#. The acid number of the entering crude fraction to the process was 150 and the naphthenic acid stream removed had an acid number of 210.

EXAMPLE 2

A crude naphthenic acid containing fraction, 29272#, was introduced into line 14. This fraction is a distillation tops material or the accumulation of the material from line 68 of the previous example. The fraction contained 9074.3# naphthenic acid, 11416.0# neutral oils (unsaps), 878.2# water and 7903.4# phenolics. The fraction was at a temperature between 60° and 120° F. and a pressure between 50 and 75 PSIA. To this fraction was added a mixture of sodium and potassium hydroxide, 2648#, of which 40% was potassium hydroxide. The mixture was at a temperature of between 60° and 90° F. and a corresponding pressure between 50 and 75 PSIA. Of the mixture, 1324# was water. These were introduced and mixed in a mixing vessel 16 at atmospheric pressures and at temperatures ranging from 80° to 140° F. The mixed stream was heated in heat exchanger 38 to temperatures within the range of 285° to 300° F. and the pressure was raised to between 20 and 30 PSIA. To the heated stream was added the recycle stream 48, 127680#, which is a portion of the material from preflash vessel 40. The stream introduced to the preflash vessel 40 is maintained at temperatures between 390° and 400° F. The pressure within the preflash vessel 40 is between 11 and 12.3 PSIA or a slight vacuum. Removed overhead by line 54, 11168.7#, comprises water, 2070.8#, and neutral oil 5137.2# as well as phenolics, 3556.5# and some naphthenic acid, 404.2#. The bottom stream, 28752#, is removed by line 60 and introduced with a falling film evaporator 62 at temeratures within the range of 480° to 500° F. and a pressure of between 0.2 and 0.77 PSIA. The material removed in vacuum line 64 and condensed, 10379#, contains neutral oils (unsaps), 5151.7#, naphthenic acid, 765.8#, phenolics, 4329.9# and only a small amount of water, 132.4#. The naphthenate stream removed from the flash vessel 62 is essentially all naphthenate, 7904.3#, containing some neutral oils (unsaps), 129.1#, and phenolics, 17#. This stream may be stored or preferably is quenched with water, 16624#, and acidified with sulfuric acid, 1986#, of which water, 496.5#, is a part of the solution. The acidified mixture, 138957#, is introduced into a decanter 80 and the acid brine is removed by line 82, 19934#, which is mostly water. A purified naphthenic acid stream is removed from second vessel 90 by line 94, 8472#, which is essentially naphthenic acid, 7904.3#, containing water, 423.6#, neutral oils (unsaps), 127.1# and a small amount of phenolics, 16.9#. The acid number of the entering crude fraction to the process was 100 and the naphthenic acid stream removed had an acid number over 300.

All values of the material balance are given in pounds (#) in the foregoing examples. Acid numbers are obtained by titrating the sample with potassium hydroxide (KOH) to a break point according to ASTM D-664-58 test procedure entitled "Neutralization Number by Potentiometric Titration" and recording the acid number in terms of milligrams (mg) of KOH per gram of sample. It is understood that the examples are exemplary only and changes may be made.

We claim:

1. A process for treating a naphthenic fraction containing phenolics, neutral oils and sulfur compounds in the production of naphthenic acid which comprises:
   mixing with the naphthenic fraction a blend of sodium and potassium hydroxide in an amount sufficient to form a naphthenate salt of between 65% to 90% of the naphthenic acid present in the fraction, wherein the potassium hydroxide is at least 35% of the blend, to form a moist naphthenate stream;
   flashing water from the moist naphthenate stream at a temperature above 360° F. to produce a dewatered naphthenate stream;
   flashing the neutral oils, phenolics and sulfur compound contaminants from the dewatered naphthenate stream;
   and recovering said naphthenic acid having an acid number greater than 300.

2. A process according to claim 1 wherein said contaminants are flashed at temperatures between about 480° and 500° F.

3. A process according to claim 1 wherein the flashing of water is from a thin film regime.

4. A process according to claim 3 wherein the flashing of the contaminants is in a falling film evaporator.

5. A process for the recovery of naphthenic acids from a naphthenic acid containing fraction which comprises:
   mixing a mixture of sodium and potassium hydroxide with a naphthenic acid containing fraction in an amount sufficient to form an alkali metal naphthenate of 70% to 80% of the naphthenic acid, potassium hydroxide being from 40% to 50% of the hydroxide mixture, to form a water containing moist naphthenate stream;
   flashing water from said moist naphthenate stream at a temperature above 360° F. to produce a dewatered naphthenate stream;
   flashing neutral oils, phenolics and sulfur compound contaminants from the dewatered naphthenate stream to form a naphthenate stream;
   acidifying said naphthenate stream to produce the naphthenic acids; and
   recovering said naphthenic acids having acid numbers greater than 300.

6. A process according to claim 5 wherein said contaminants are flashed at temperatures between about 480° and 500° F.

7. A process according to claim 5 wherein the flashing of water is from a thin film regime.

8. A process according to claim 7 wherein the flashing of the contaminants is in a falling film evaporator.

* * * * *